United States Patent [19]
Gregory et al.

[11] Patent Number: 5,283,257
[45] Date of Patent: Feb. 1, 1994

[54] METHOD OF TREATING HYPERPROLIFERATIVE VASCULAR DISEASE

[75] Inventors: Clare R. Gregory, Davis; Randall E. Morris, Los Altos, both of Calif.

[73] Assignee: The Board of Trustees of the Leland Stanford Junior University, Stanford, Calif.

[21] Appl. No.: 911,681

[22] Filed: Jul. 10, 1992

[51] Int. Cl.$^5$ ............................................. A61K 31/35
[52] U.S. Cl. .................................................... 514/458
[58] Field of Search ........................................ 514/456

[56] References Cited

U.S. PATENT DOCUMENTS 3,705,946 12/1972 Dyke et al. .................... 514/473
3,880,995 4/1975 Janeo .............................. 514/456

*Primary Examiner*—S. J. Friedman
*Attorney, Agent, or Firm*—Gary R. Fabian; Peter J. Dehlinger

[57] ABSTRACT

This invention provides a method of preventing or treating hyperproliferative vascular disease in a mammal by administering an amount of mycophenolic acid effective to inhibit intimal thickening.

9 Claims, 3 Drawing Sheets

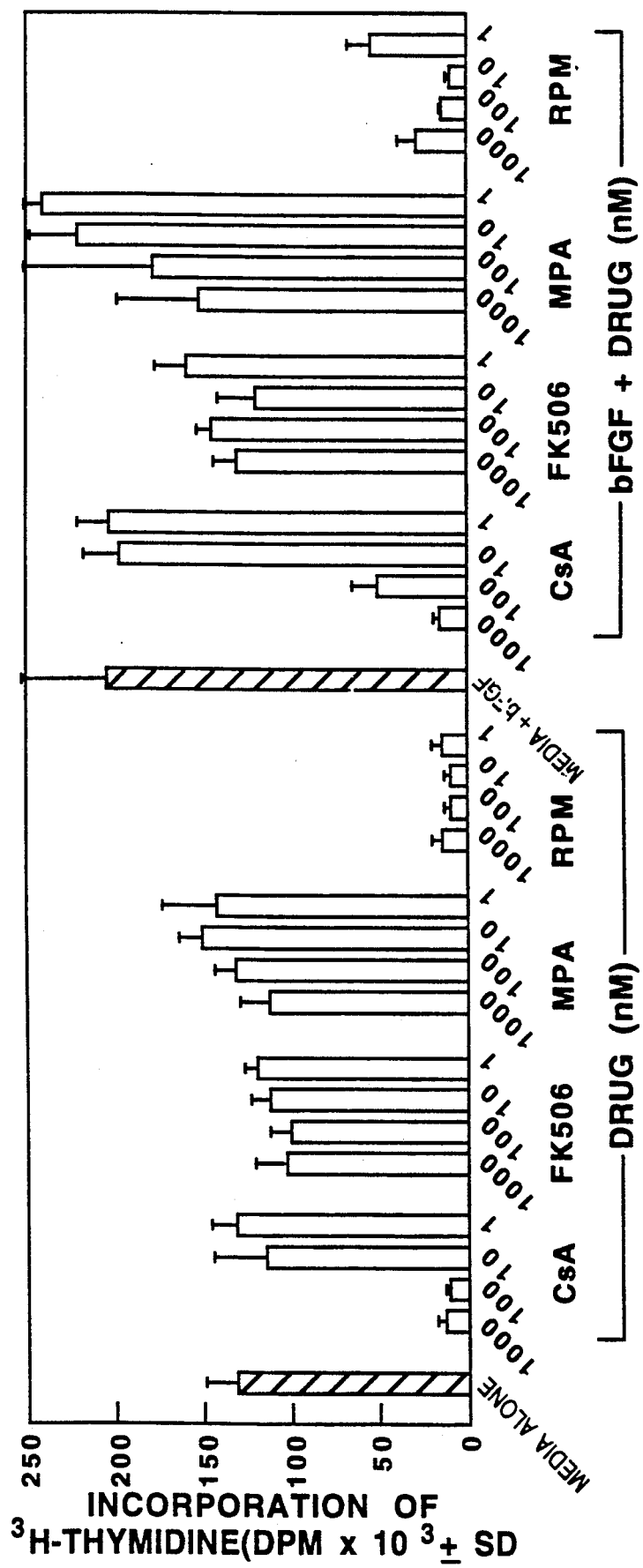
Fig. 2 con't

METHOD OF TREATING HYPERPROLIFERATIVE VASCULAR DISEASE

FIELD OF THE INVENTION

The present invention relates to the use of mycophenolic acid for the treatment of hyperproliferative vascular disease in a mammal, including intimal smooth muscle cell hyperplasia, restenosis, and vascular occlusion.

REFERENCES

Allison, A. C., et al., U.S. Pat. No. 4,786,637, issued 22 November 1988.
Califf, R., et al., in *Textbook of Interventional Cardiology*, E. Topol, Ed., (W. B. Saunders Co., Philadelphia, 1990), pages 363-394.
Calne, R., European Patent Application 401,747.
Chevru, A., Surg. Gynecol. Obstet. 171:443 (1990).
Clowes, A. W., Lab. Invest. 32:339 (1975).
Clowes, A. W., Circ. Res. 56:139 (1985).
Clowes, A. W., J. Cardiovas. Pharm. 14 (Suppl. 6):S12 (1989).
Darius, H., Eur. Heart J. 12 (Suppl.):26 (1991).
Davies, P. F., Atherosclerosis Lab. Invest. 55:5 (1986).
de Vries, C., Eur. Heart J. 12 (Suppl.):386 (1991).
Demke, D., Brit. J. Haematol 76 (Suppl.):20 (1990).
Eugui, E., et al., Scand. J. Immunol. 33:161 (1991).
Evans, R. G., JAMA 265:2382 (1991). Ferns, G. A., Circulation 80 (Suppl.):184 (1989). Ferns, G. A., Am. J. Path. 137:403 (1990). Ferns, G. A., Science 253:1129 (1991). Fingerle, J., Arteriosclerosis 10:1082 (1990). Fishman, J. Lab. Invest. 32:339 (1975). Forrester, J., J. Am. Coll. Cardiol. 1-7:758 (1991). Geisterfer, A. T. T., et al., Circ. Res. 62:749-756 (1988). Gellman, J., J. Am. Coll. Cardiol. 17:251 (1991). Gorman, R. R., et al., Prostaglandins 26(2):325-342 (1983). Gottlieb, N., J. Am. Coll. Cardiol. 17 (Suppl. A): A (1991). Graham, L. M., et al., J. Surg. Res. 46:611-615 (1989). Hardoff, R., J. Am. Coll. Cardiol. 15:1486 (1990). Haudenschild, C., Lab. Invest. 4-1:407 (1979). Ip, J. H., et al., JACC 15(7):1667-1687 (1990). Jonasson, L., Proc. Natl. Acad. Sci. 85:2303 (1988). Lee, H-Y., et al., Cancer Research 45:5512-5520 (1985). Manderson, J., Arterio. 9:289 (1989). Martel, R., Can J. Physiol. Pharm. 55:48 (1977). Morris, R., Med. Sci. Res. 17:877 (1989). Morris, R. E., Transplantation Rev. 6:39 (1992). Nelson, P. H., et al., U.S. Pat. No. 4,686,234, issued 11 August 1987. Nelson, P. H., et al., U.S. Pat. No. 4,727,069, issued 23 February 1988. Nelson, P. H., et al., U.S. Pat. No. 4,753,935, issued 28 June 1988. Nye, E., Aust. N.Z. J. Med. 20:549 (1990). Ohsugi, et al., Cancer Res. 36:2923-2927 (1976). Okamoto, S., Circulation 82 (Suppl.):428 (1990). Papadimitriou, J., et al., Ultrastruct. Pathol. 343 (1989). Payne, J. E., et al., Aust. N.Z. J. Surg. 61:619-625 (1991). Pepine, C., Circulation 81:1753 (1990). Reidy, M., Lab. Invest. 59:36 (1988). Sahni, R., Circulation 80 (Suppl.):65 (1989). Sakaguchi, K., et al., Cancer Research 35:1643-1648. Sokoloski, J., et al., Cancer Res. 46:2314 (1986). Schwartz, S. M., Human Pathology 18:240 (1987). Staruch, M., FASEB 3:3411 (1989). Sweeney, M. J., et al., Cancer Res. 32:1795-1802 (1972). Sehgal, S. N., et al., U.S. Pat. No. 3,929,992, issued 30 December 1975. Wynalda, M.A., et al., Prostaglandins 26(2):311-324 (1983). Yabe, Y., Circulation 80 (Suppl.):260 (1989).

BACKGROUND OF THE INVENTION

Partial blockage of the blood vessels leading to the heart is one cause of heart disease. More severe blockage of blood vessels often leads to hypertension, ischemic injury, stroke, or myocardial infarction. Vascular occlusion is typically preceded by vascular stenosis which can be the result of intimal smooth muscle cell hyperplasia. One underlying cause of intimal smooth muscle cell hyperplasia is vascular smooth muscle injury and disruption of the integrity of the endothelial lining. Occlusive coronary atherosclerosis remains the major cause of mortality and morbidity in industrialized countries.

Arterial intimal thickening after injury is the result of the following series of events: 1) initiation of smooth muscle cell (SMC) proliferation within hours of injury, 2) SMC migration to the intima, and 3) further SMC proliferation in the intima with deposition of matrix (Clowes, et al., 1989). Investigations of the pathogenesis of intimal thickening following arterial injury have shown that platelets, endothelial cells, macrophages and smooth muscle cells release paracrine and autocrine growth factors (such as platelet derived growth factor (PDGFa), epidermal growth factor, insulin-like growth factor, and transforming growth factor and cytokines that result in the smooth muscle cell proliferation and migration (Ip, et al.). T-cells and macrophages also migrate into the neotima (Haudenschild; Clowes, 1985; Clowes, 1989; Manderson; Forrester). This cascade of events is not limited to arterial injury, but also occurs following injury to veins and arterioles. The overall disease process can be termed a hyperproliferative vascular disease because of the etiology of the disease process.

Vascular injury causing intimal thickening can be broadly categorized as being either biologically or mechanically induced. One of the most commonly occurring forms of biologically mediated vascular injury leading to stenosis is Atherosclerosis. The migration and proliferation of vascular smooth muscle plays a crucial role in the pathogenesis of atherosclerosis. Atherosclerotic lesions include massive accumulation of lipid laden "foam cells" derived from monocyte/macrophage and smooth muscle cells. Formation of "foam cell" regions is associated with a breech of endothelial integrity and basal lamina destruction. Triggered by these events, restenosis is produced by a rapid and selective proliferation of vascular smooth muscle cells with increased new basal lamina (extracellular matrix) formation and results in eventual blocking of arterial pathways (Davies).

Mechanical injuries leading to intimal thickening result following balloon angioplasty, vascular surgery, transplantation surgery, and other similar invasive processes that disrupt vascular integrity. Although balloon angioplasty can dilate arterial stenosis effectively, restenosis occurs in 30-40% of patients after 6 months (Califf, et al., 1990). Intimal thickening following balloon catheter injury has been studied in animals as a model for arterial restenosis that occurs in human patients following balloon angioplasty. De-endothelialization with an intraarterial catheter, which dilates an artery, injures the innermost layers of medial smooth muscle and may even kill some of the innermost cells (Schwartz; Fingerle; Clowes, 1975, Ferns, 1989, Reidy, 1988).

Injury to the innermost layers of medial smooth muscle is followed by a proliferation of the medial smooth muscle cells, after which many of them migrate into the intima through fenestrae in the internal elastic lamina and proliferate to form a neointimal lesion.

Typically, vascular stenosis can be detected and evaluated using angiographic or sonographic imaging techniques (Evans) and is often treated by percutaneous transluminal coronary angioplasty (balloon catheterization). Within a few months following angioplasty, however, the blood flow is reduced in approximately 30-40 percent of treated patients as a result of restenosis caused by a response to mechanical vascular injury suffered during the angioplasty procedure (Pepine; Hardoff).

In an attempt to prevent restenosis or reduced intimal smooth muscle cell proliferation following angioplasty, numerous pharmaceutical agents have been employed clinically, concurrent with or following angioplasty. Most pharmaceutical agents employed in an attempt to prevent or reduce the extent of restenosis have been unsuccessful. The following list identifies several of the agents for which favorable clinical results have been reported: lovastatin (Sahni; Gellman); thromboxane $A_2$ synthetase inhibitors such as DP-1904 (Yabe); eicosapentanoic acid (Nye); ciprostene (a prostacyclin analog) (Demke; Darius); trapidil (a platelet derived growth factor) (Okamoto); angiotensin converting enzyme inhibitors (Gottlieb); low molecular weight heparin (de Vries); and 5-(3'-pyridinylmethyl)-benzofuran-2-carboxylate (Gorman, et al.; Payne, et al.; Wynalda, et al.; Graham, et al.).

The use of balloon catheter induced arterial injury in a variety of mammals has been developed as a standard model of vascular injury that will lead to intimal thickening and eventual vascular narrowing (Chevru; Fishman; Clowes, 1983; Clowes, 1991). Many compounds have been evaluated in this standard animal model in an attempt to develop better agents for preventing or reducing smooth muscle proliferation and intimal thickening.

SUMMARY OF THE INVENTION

This invention provides a method of preventing or treating hyperproliferative vascular disease in a mammal in need thereof by administering an amount of mycophenolic acid effective to inhibit intimal thickening. Administration of the mycophenolic acid can be accomplished by a number of methods including orally, parenterally, intravascularly, intranasally, intrabronchially, transdermally, rectally, or via a vascular stent impregnated with mycophenolic acid.

In addition to mycophenolic acid, a number of derivatives thereof may be useful in the practice of the present invention including morpholinoethylesters of mycophenolic acid and heterocyclic aminoalkyl esters of mycophenolic acid. Further, the form of the mycophenolic acid may also include a pharmaceutically acceptable salt.

As such, mycophenolic acid is useful, alone or in combination with other treatments, in preventing or treating intimal smooth muscle cell hyperplasia, restenosis, and vascular occlusion in a mammal, particularly following either biologically or mechanically mediated vascular injury. Biologically mediated vascular injury includes, but is not limited to, injury attributed to autoimmune disorders; alloimmune related disorders; infectious disorders including endotoxins and herpes viruses, such as cytomegalovirus; metabolic disorders such as atherosclerosis; and vascular injury resulting from hypothermia and irradiation.

Mechanically mediated vascular injury includes, but is not limited to, vascular injury caused by catheterization procedures or vascular scraping procedures such as percutaneous transluminal coronary angioplasty; vascular surgery; transplantational surgery; laser treatment; and other invasive procedures which disrupt the integrity of the vascular intima and endothelium.

The method of the present invention includes the prophylactic prevention of hyperproliferative vascular disease in a susceptible mammal and/or treatment in order to arrest the development and retard the progression of hyperproliferative vascular disease in a susceptible mammal.

Other combinations containing mycophenolic acid that are useful for preventing or treating hyperproliferative vascular disease will be apparent to one skilled in the art. These include, but are not limited to, using mycophenolic acid in combination with other antiproliferative antimetabolites or other drugs useful for the treatment of hyperproliferative diseases.

In addition to MPA, a number of molecules which inhibit inosine monophosphate dehydrogenase (IMP-DH) may be useful in the method of the present invention for suppression of intimal thickening after vascular injury. The following are exemplary of such molecules: Mizoribine (bredinin), Ribovirin, tiazofurin and selenazarfurin.

The present invention also includes a composition for the use in preventing or treating hyperproliferative vascular disease in a mammal which comprises an amount of mycophenolic acid effective to inhibit intimal thickening and a pharmaceutically acceptable carrier. The composition can be used as described above.

DETAILED DESCRIPTION OF THE INVENTION

I. Mycophenolic Acid and Hyperproliferative Vascular Disease

Figure 1:
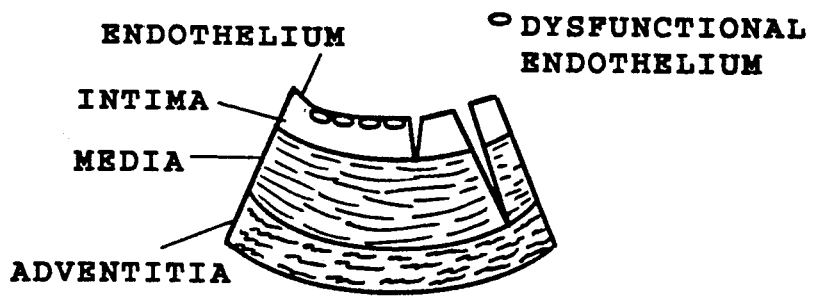
FIG. 1 shows a schematic representation of the cross-section of the carotid artery (adapted from Ip, et al.).

The effect of mycophenolic acid (MPA) on hyperproliferative vascular disease was evaluated using in vitro and in vivo standard pharmacological test procedures. The in vivo test emulates the hyperproliferative effects observed in mammals undergoing intimal smooth muscle (FIG. 1) proliferation—a common model for the development of restenosis.

A. In Vitro Analysis

Basic fibroblast growth factor (BFGF) has been shown to be a key mitogen for vascular SMCs following injury. bFGF was used to stimulate intimal smooth muscle cell proliferation in vitro (a standard pharmacological test procedure which emulates the intimal smooth muscle cell proliferation observed following vascular injury). The effects of different concentrations of cyclosporine (CsA), FK506, rapamycin (RPM), and mycophenolic acid (MPA) on bFGF's mitogenic effects on SMC were tested in vitro. The drugs were added individually to wells containing confluent cultures of rat aortic SMC made quiescent in defined serum-free media (Example 1). Twenty-four hours later, BFGF (15 μg/ml) was added and the synthesis of both RNA and DNA were measured. The results of this analysis are presented in FIG. 2.

Figure 2:
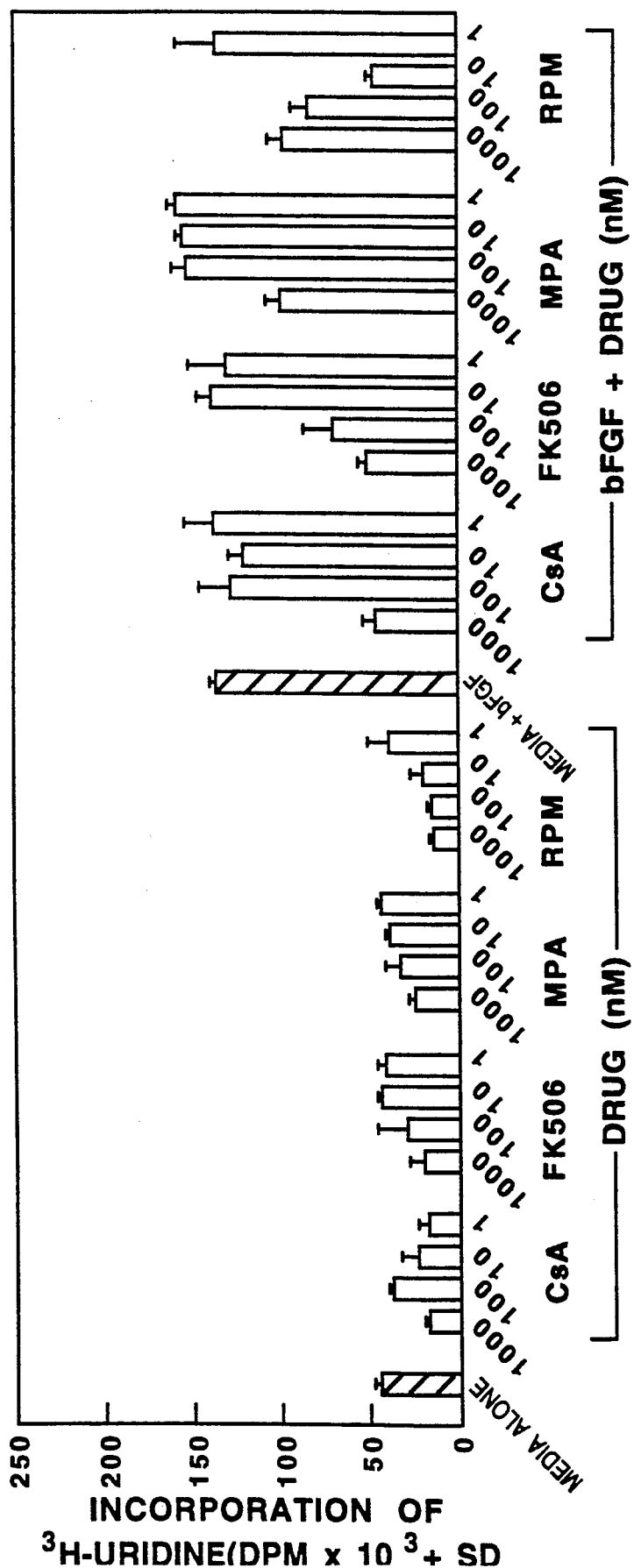
FIG. 2 shows a bar graph presenting the data which demonstrate the effects of a number of drugs on $^3$H-uridine and $^3$H-thymidine incorporation of rat aortic smooth muscle cells.

The only drug that was cytotoxic to SMC was CsA; 1000 nM caused both histopathologic abnormalities and a four-fold increase in lactate dehydrogenase levels in supernatant fluids compared to controls. RPM inhibited significantly basal- and bFGF-stimulated SMC DNA synthesis (FIG. 2). Only high concentrations of CsA, FK506 and MPA were inhibitory.

B. In Vivo Analysis

CsA, FK506, MPA, RPM, and rapamycin plus mycophenolic acid (RPM/MPA) were evaluated in an in vivo standard pharmacological test procedure that emulates the vascular injury suffered and restenosis that develops following percutaneous transluminal coronary angioplasty in humans (Chevru; Fishman; Haudenschild; Clowes, 1983; Clowes, 1989; Ferns, 1991).

To examine the possible efficacy of these agents on restenosis, the left carotid arteries of male Sprague Dawley rats were injured by three passes with an inflated 2 Fr balloon catheter on day 0; the right, uninjured carotid arteries were negative controls (Example 2). Rats were treated daily starting after balloon injury (days 0-13) with CsA (6 or 3 mg/kg/d IP, N =6/group), FK506 (4 mg/kg/d PO, N =5), MPA (40 mg/kg/d PO, N =8), RPM (1.5, 3 or 6 mg/kg/d IP, N =5) or combined treatment (1.5 mg/kg/d of RPM plus 40 mg/kg/d of MPA, N =5). One rat in each group served as a balloon-injured, no treatment positive control. All rats were euthanized on day 14 and midportions of both carotid arteries were excised, frozen and sectioned for histopathologic, morphometeric, and immunohistochemical assays. The results of quantitation of intimal and media thickening are presented in Table 1 (Example 2) and FIG. 3.

Figure 3:
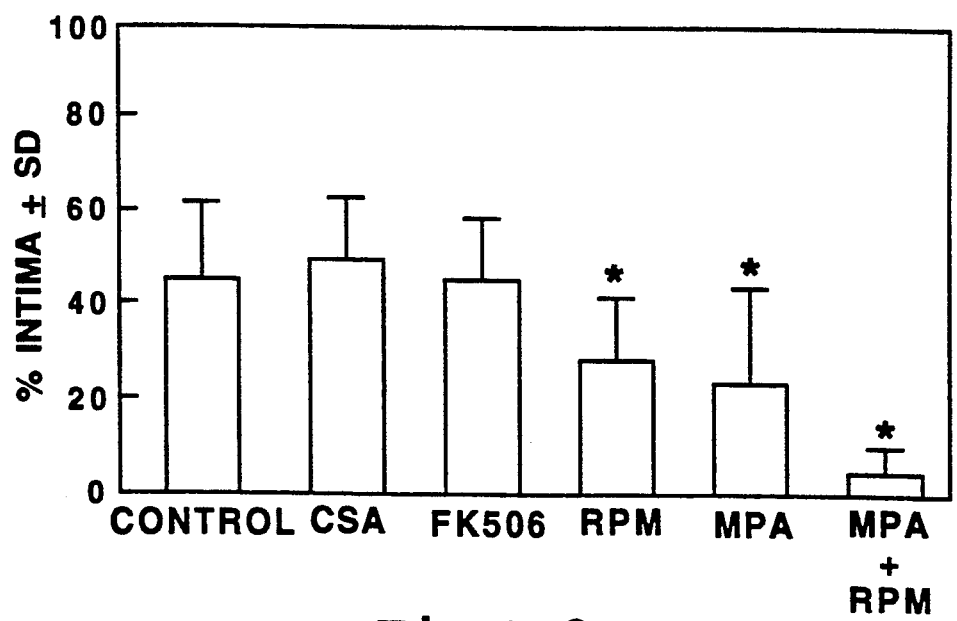
FIG. 3 shows a bar graph presenting the data for intima percent of rat arteries 14 days after balloon catheter injury with a variety of drug treatments.

In the rats treated with 6 mg/kg of CsA, the injured arteries became thrombosed or were completely occluded by the thickened intima. A dose of CsA (3 mg/kg) caused thrombosis of two of the injured vessels and failed to reduce the mean intimal percent (morphometric quantitation of: (intima area/intima area+media area)×100) in the remaining 4 arteries (p=0.801 vs. control) (Table 1; FIG. 3)). Treatment of FK506 did not decrease intimal percent compared to untreated controls (p=0.6847), but treatment with MPA decreased intimal percent by 52% (p=0.0254) (Table 1). A RPM dose of 1.5 mg/kg decreased intimal percent by 45% (p=0.0338) (FIG. 3). This was the maximally effective dose in this study, since higher doses of RPM did not result in further reduction in intimal thickness (p>0.5). The response of the arterial wall to balloon injury was most effectively suppressed by combined treatment with RPM plus MPA; the mean intimal percent for this group was reduced by 97% (p=0.000085). The uninjured right carotid arteries in rats from all groups were histopathologically normal.

The results indicate that in vivo the following drugs, and combinations, are effective in preventing restenosis that develops following percutaneous transluminal coronary angioplasty: RPM/MPA>MPA>RPM. The results demonstrate that MPA alone is useful in preventing or treating hyperproliferative vascular disease. Specifically, mycophenolic acid is useful in preventing or treating intimal smooth muscle cell hyperplasia, restenosis, and vascular occlusion in a mammal, particularly following either biologically or mechanically mediated vascular injury, or under conditions that would predispose a mammal to suffering such a vascular injury.

C. In Vivo versus In Vitro Results with MPA

Although MPA blocks intimal thickening, it does not appear to block DNA or RNA production in BFGF stimulated SMC (see above). Accordingly, the in vitro results in no way predicted that it would be effective in vivo to treat hyperproliferative vascular disease with mycophenolic acid.

Experiments performed in support of the present invention indicate that mycophenolic acid's inhibition of inosine monophosphate dehydrogenase (IMP-DH) is responsible for its effects on suppression of intimal thickening. Immune cells depend solely on the de novo biosynthetic pathway for guanosine synthesis, i.e., there is no active salvage pathway. MPA inhibits DNA synthesis in activated immune cells, such as monocytes, relatively selectively: it prevents guanosine synthesis by blocking inosine monophosphate dehydrogenase activity (Eugui, et al.). The resistance of fibroblasts and SMC to antiproliferative effects of MPA, when these cells are stimulated in vivo by BFGF (FIG. 2), may be explained by MPA having no effect on nucleic acid salvage pathways in SMC.

Accordingly, unlike RPM, it is not likely that MPA inhibits intimal thickening after balloon injury by acting on SMC directly to prevent their proliferation. Experiments performed in support of the present invention suggest that the effects of MPA on monocytes may be indirectly responsible for its efficacy in preventing restenosis. In particular, low levels of guanosine caused by inhibition of IMP-DH may be responsible for the inability of monocytes to synthesize DNA and adhesion molecules. Adhesion molecules are typically glycosylated proteins and the glycosylation of these proteins proceeds through guanosine linked sugars.

In view of the above results, a number of molecules which inhibit IMP-DH, in addition to MPA, may be useful in the method of the present invention for suppression of intimal thickening after vascular injury. Examples of other such molecules, which inhibit IMP-DH, include but are not limited to the following: Mizoribine (bredinin) (Sakaguchi, et al.); and Riboviran, tiazofurin and selenazarfurin (Lee, et al.).

Neither treatment with RPM nor MPA alone completely prevented intimal thickening after balloon catheter arterial injury in this study. This suggests that there are specific pathways responsible for vascular remodeling after mechanical injury that are resistant to the individual actions of RPM or MPA at the doses used. Accordingly, this result suggests that MPA, alone or in combination with other IMP-DH inhibitors, may be particularly useful in treatment of intimal thickening when combined with other active agents, where the other agents affect the RPM-like pathway.

II. Mycophenolic Acid

Mycophenolic acid is an antibiotic substance which is produced by *Penicillium brevi-compactum* and related species (*The Merk Index,* Tenth Edition, 1983). A number of forms of mycophenolic acid have been derived which are useful in methods of treating autoimmune disorders, psoriasis and other inflammatory diseases. In the present application, the term "mycophenolic acid" is used to refer to mycophenolic acid itself and to pharmaceutically active derivatives thereof. A number of derivatives of mycophenolic acid are taught in Ohsugi, et al., Sweeney, et al., and U.S. Pat. Nos. 4,686,234, 4,727,069, 4,753,935, 4,786,637, all herein incorporated by reference, as well as the pharmaceutically acceptable salts thereof.

Typically, after introduction of derivatives of mycophenolic acid into the body, the derivatives are converted to mycophenolic acid. Accordingly, the treatment methods of the present invention include the delivery of any such derivatives of mycophenolic acid into a mammalian system, in order to inhibit intimal thickening, which, when the derivative is administered to the mammalian host, results in the therapeutic form of the derivative being mycophenolic acid—regardless of the derivative form by which it was originally introduced into the mammalian host.

In addition to structurally modified variant compounds of mycophenolic acid, a number of pharmaceutically acceptable salts of these compounds are also available. Such pharmaceutically acceptable salts include any salt derived from bases or acids, where the base or acid is inorganic or organic. Inorganic acids include, but are not limited to, hydrochloric acid, sulfuric acid and phosphoric acid. organic acids include, but are not limited to, acetic acid, pyruvic acid, succinic acid, oxalic acid and maleic acid. Inorganic bases include, but are not limited to, sodium, lithium, potassium, calcium, magnesium and ammonium. Organic bases include, but are not limited to, primary, secondary and tertiary amines.

Other variant forms of mycophenolic acid can be tested for use in the method of the present invention as described above, and as described in Examples 1 and 2. Typically, mycophenolic acid is administered to a mammal in need of treatment at a therapeutically effective amount of the compound.

III. Pharmaceutical Preparations of Mycophenolic Acid

Mycophenolic acid when employed in the prevention or treatment of hyperproliferative vascular disease, can be formulated neat or with a the addition of a pharmaceutical carrier. The pharmaceutical carrier may be solid or liquid. The formulation is then administered in a therapeutically effective dose to a mammal in need thereof.

A solid carrier can include one or more substances. The carrier may also act to provide flavoring agents, lubricants, solubilizers, suspending agents, filters, glidants, compression aids, binders or tablet-disintegrating agents. The carrier can also function as an encapsulating material. In powders, the carrier is typically a finely rendered solid which is in a mixture with the finely rendered active ingredient—mycophenolic acid. In tablet form, a carrier with the necessary compression properties is mixed with the mycophenolic acid in suitable proportions. The mixture is then compacted in the shape and size desired. The powders and tablets preferably contain up to 99% of the active ingredient. A number of suitable solid carriers are available, including, but not limited to, the following: sugars, lactose, dextrin, starch, gelatin, calcium phosphate, magnesium stearate, talc, polyvinylpyrrolidone, low melting waxes, ion exchange resins, cellulose, methyl cellulose, and sodium carboxymethyl cellulose.

Liquid carriers can be used in the preparation of elixirs, solutions, emulsions, syrups, suspensions and pressurized compositions. The mycophenolic acid is dissolved or suspended in a pharmaceutically acceptable liquid carrier such as water, an organic solvent, a mixture of both, or pharmaceutically accepted oils or fats. The liquid carrier can contain other suitable pharmaceutical additives including, but not limited to, the following: solubilizers, flavoring agents, suspending agents, emulsifiers, buffers, thickening agents, colors, viscosity regulators, preservatives, sweeteners, stabilizers and osmolarity regulators. Suitable examples of liquid carriers for oral and parenteral administration of mycophenolic acid preparations include water (partially containing additives as above, e.g., cellulose derivatives, preferably sodium carboxymethyl cellulose solution), alcohols (including monohydric alcohols and polyhydric alcohols, e.g., glycols) and their derivatives, and oils (e.g., fractionated coconut oil and arachis oil).

For parenteral administration of mycophenolic acid the carrier can also be an oily ester such as ethyl oleate and isopropyl myristate. Sterile carriers are useful in sterile liquid form compositions for parenteral administration.

Sterile liquid pharmaceutical compositions, solutions or suspensions can be utilized by, for example, intraperitoneal injection, subcutaneous injection, or intravenously. Mycophenolic acid, can be also be administered intravascularly or via a vascular stent impregnated with mycophenolic acid, during balloon catheterization to provide localized effects immediately following injury.

Mycophenolic acid-containing compositions of the present invention can also be administered orally either in liquid or solid composition form.

The liquid carrier for pressurized compositions can be halogenated hydrocarbon or other pharmaceutically acceptable propellent. Such pressurized compositions may also be lipid encapsulated for delivery via inhalation. For administration by intranasal or intrabronchial inhalation or insufflation, mycophenolic acid may be formulated into an aqueous or partially aqueous solution, which can then be utilized in the form of an aerosol.

Mycophenolic acid can be rectally administered in the form of a conventional suppository. Alternatively, the drug may be administered transdermally through the use of a transdermal patch containing the active compound and a carrier that is inert to the active compound, is non-toxic to the skin, and allows delivery of the agent for systemic absorption into the blood stream via the skin. Carriers for transdermal absorption may include pastes, e.g., absorptive powders dispersed in petroleum or hydrophilic petroleum containing the active ingredient with or without a carrier, or a matrix containing the active ingredient; creams and ointments, e.g., viscous liquid or semi-solid emulsions of either the oil-in-water or the water-in-oil type; gels and occlusive devices. Preparations of mycophenolic acid, may be administered topically as a solution, cream, or lotion, by formulation with pharmaceutically acceptable vehicles containing the active compound.

The dosage requirements for treatment with mycophenolic acid vary with the particular compositions employed, the route of administration, the severity of the symptoms presented, the form of mycophenolic acid and the particular subject being treated. Based on the results obtained in the standard pharmacological test procedures, projected daily intravenous dosages of mycophenolic acid, when administered as the sole active compound, would be in the range of approximately 500–4000 mg/d, p.o.

Typically, treatment with mycophenolic acid is initiated with small dosages: less than the optimum dose. The dosage is increased until the optimum effect, under the conditions of treatment, is reached. Precise dosages for oral, parenteral, intravascular, intranasal, intrabronchial, transdermal, or rectal administration are determined by the administering physician based on experience with the individual subject treated.

In general, mycophenolic acid is administered at a concentration that affords effective results without causing any harmful or deleterious side effects. Such a concentration can be achieved by administration of either a single unit dose, or by the administration of the dose divided into convenient subunits at suitable intervals throughout the day.

IV. Utility

Mechanical injuries leading to intimal thickening result following balloon angioplasty, vascular surgery, transplantation surgery, and other similar invasive processes that disrupt vascular integrity. Injury to the innermost layers of medial smooth muscle is followed by a proliferation of the medial smooth muscle cells, after which many of them migrate into the intima through fencstrac in the internal elastic lamina and proliferate to form a neointimal lesion.

Partial blockage of the blood vessels leading to the heart is one cause of heart disease. More severe blockage of blood vessels often leads to hypertension, ischemic injury, stroke, or myocardial infarction. Vascular occlusion is typically preceded by vascular stenosis which can be the result of intimal smooth muscle cell hyperplasia. One underlying cause of intimal smooth muscle cell hyperplasia is vascular smooth muscle injury and disruption of the integrity of the endothelial lining.

Typically, vascular stenosis can be detected and evaluated using angiographic or sonographic imaging techniques (Evans) and is often treated by percutaneous transluminal coronary angioplasty (balloon catheterization). Within a few months following angioplasty, however, the blood flow is reduced in approximately 30–40 percent of treated patients as a result of restenosis caused by a response to mechanical vascular injury suffered during the angioplasty procedure (Pepine; Hardoff).

In an attempt to prevent restenosis or reduced intimal smooth muscle cell proliferation following angioplasty, numerous pharmaceutical agents have been employed clinically, concurrent with or following angioplasty. Most pharmaceutical agents employed in an attempt to prevent or reduce the extent of restenosis have been unsuccessful.

Experiments performed in support of the present invention indicate that mycophenolic acid is nontoxic and an effective agent, in vivo, for preventing intimal smooth muscle thickening following arterial injury. The use of mycophenolic acid may provide therapeutic strategies for the control of hyperproliferative vascular disease following heart transplantation. The present invention generally relates to the use of mycophenolic acid for the treatment of hyperproliferative vascular disease in a mammal, including intimal smooth muscle cell hyperplasia, restenosis, and vascular occlusion.

The following examples illustrate, but in no way are intended to limit the present invention.

Materials and Methods

The immunosuppressive agents were obtained from the following sources: cyclosporine (CsA) (Sandoz, Inc., East Hannover, N.J.), FK506 (Fujisawa, Inc., Usaka, Japan), rapamycin (RPM) (Wyeth-Ayerst, Inc., Princeton, N.J.), and mycophenolic acid (MPA) (Sigma Chemical Co., St. Louis, Mo.).

EXAMPLE 1

Treatment of Rat Aortic Smooth Muscle Cell Cultures with MPA

The immunosuppressive agents cyclosporine (CsA), FK506, rapamycin (RPM), and mycophenolic acid (MPA), were compared in vitro for antiproliferative effects against vascular smooth muscle cells. Rat aortic smooth muscle cells were grown in culture essentially as described by Geisterfer, et al. Briefly, rat smooth muscle cells were maintained in a 1:1 mixture of defined Eagle's medium (DEM) (Gibco BRL, Gaithersburg Md.) and Ham's F12 medium (Gibco BRL) with 10% fetal calf serum, penicillin (100 U/mL), streptomycin (100 mg/ml) and 25 ML Hepes at pH 7.4. Cells were incubated at 37° C. in a humidified atmosphere of 5% $CO_2$ with media changes every 2–3 days. Each compound tested was diluted with an appropriate solvent to obtain a 1 mm stock solution.

Ethanol was used as the solvent for rapamycin, methanol for FK506, dimethylsulfoxide (DMSO) for mycophenolic acid and 20% "TWEEN 80" (Sigma, St. Louis Mo.) in ethanol was the vehicle for cyclosporin A. Test concentrations of drug were obtained by diluting appropriate concentrations of stock solution with serum free media.

Multi-well plate cultures of smooth muscle cells were maintained in defined serum free media containing 1:1 DEM and Ham's F12 medium, insulin ($5 \times 10^{-7}$ M), transferrin (5 $\mu$g/mL), and ascorbate (0.2 MM) for 72 hours before the addition of test compounds. After 72 hours, dilutions of the test compounds were added to the smooth muscle cell culture and media mixtures.

After 24 hours BFGF (basic fibroblast growth factor (Gibco BRL)) was added at a concentration of approximately 15 $\mu$g/ml.

For the measurement of DNA or RNA synthesis, $^3$H-thymidine or $^3$H-uridine, respectively, was added at 12 hours after the growth factor was added, and the cells were harvested at 18 hours. The amount of incorporated radioactive label was measured using a scintillation counter.

The data for the effects of CsA, FK506, RPM, and MPA on $^3$H-thymidine and $^3$H-uridine incorporation in rat aortic smooth muscle cells (SMC) are shown in FIG. 2. In the figure: each bar represents the mean dissociations per minute of four cultures; BFGF indicates the addition of 15 $\mu$g/ml of basic FGF; and for CsA, FK506, RPM, and MPA, the concentrations of the addition of each drug are given at the bottom of each panel of the figure (1000 nM, 100 nM, 10 nM or 1 nM).

The only drug that was cytotoxic to SMC was CsA; 1000 nM caused both histopathologic abnormalities and a four-fold increase in lactate dehydrogenase levels in supernatant fluids compared to controls. RPM inhibited significantly basal- and bFGF-stimulated SMC DNA synthesis (FIG. 2). Only high concentrations of the other drugs were inhibitory.

EXAMPLE 2

Balloon Catheter Injury Assays for Intimal Thickening

Intimal smooth muscle proliferation was produced by balloon catheter injury to the left carotid artery of groups of 6, male Sprague-Dawley rats. Endothelial denudation and vascular injury were achieved in the left carotid arteries of male Sprague-Dawley rats. A balloon catheter (2 French Fogarty, Edwards Laboratories, Santa Anna, Calif.) was passed through the external carotid artery into the aorta. The balloon was then inflated with an amount of water sufficient to distend the common carotid artery and was then pulled back to the external carotid artery. The inflation and pull back were repeated three times. This procedure leads to complete denudation of the endothelium throughout the common carotid artery, and also some injury typically occurs to the medial smooth muscle cells.

During a 14-day post-operative period (day 0 to day 13), these rats were divided into 6 groups and treated daily with rapamycin (1.5 mg/kg/d, N=5/group; i.p.), FK506 (4 mg/kg/d, N=5/group; p.o.), MPA (40 mg/kg/d, N=8/group; p.o.), cyclosporin A (3 mg/kg/d, N=6/group; i.p.), or rapamycin plus mycophenolic acid (1.5 mg/kg/d of RPM plus 40 mg/kg/d of MPA, N=5/group: i.p., and p.o., respectively).

An injured group not treated with any drug was used as an injured control to establish the amount of intimal groups in the absence of treatment. The right carotid was used as an uninjured control in all groups.

After the 14 day period, the rats were sacrificed, the carotids removed. The mean areas of the intima, media and total blood vessel wall were measured by morphometry. The injured artery was also examined using histopathologic assays. Results are presented as an intima percent, expressed as follows:

$$\frac{\text{area of intima}}{\text{area of intima} + \text{area of media}} * 100$$

Table 1 shows the data obtained in the above experiment.

TABLE 1

|  | Control | RPM | Percent Intime FK506 | MPA | CsA | MPA-RPM |
|---|---|---|---|---|---|---|
|  | 60 | 19 | 33 | 0 | 60.7 | 0 |
|  | 65 | 50 | 26 | 16 | 60.7 | 8 |
|  | 65 | 34 | 55 | 20 | 47.8 | 0 |
|  | 28 | 9 | 58 | 51 | 34.8 | 0 |
|  | 54 | 21 | 52 | 32 |  | 0 |
|  | 33 |  |  | 0 |  |  |
|  | 35 |  |  | 45.7 |  |  |
| mean | 48.57143 | 26.6 | 44.8 | 23.52857 | 51 | 1.6 |
| sd | 16.07127 | 15.82087 | 14.34225 | 20.38927 | 12.39435 | 3.577709 |
| p VALUE, T-Test for two means, vs CONTROL | | 0.0338 | 0.6847 | 0.0254 | 0.801 | 0.000085 |

The data presented in Table 1 are also represented in FIG. 3. In the figure, the intima percent of 5 to 8 rat carotid arteries 14 days after balloon catheter injury are shown. All drugs were administered starting the day of surgery and for 13 additional days. The bars in FIG. 3 represent the following: control, untreated and uninjured rats; CsA, cyclosporin at 3 mg/kg/IP; FK506, at 4 mg/kg/PO; RPM, rapamycin at 1.5 mg/kg/IP; MPA, mycophenolic acid at 40 mg/kg/PO; and RPM +MPA at 1.5 mg/kg/IP and 40 mg/kg/PO, respectively. The asterisk shows a significant value at p less than or equal to 0.05 using the Student Tetest (two-tailed) for two means.

In vivo, combined RPM +MPA treatment resulted in an approximately 97% decrease in mean percentage of intimal thickening, relative to the untreated control group. Separate RPM and MPA treatment resulted in approximately 45% and 52% decrease in mean percentage of intimal thickening, respectively, relative to the untreated control group. CsA and FK506 had little or no effect on smooth muscle intimal thickening.

While the invention has been described with reference to specific methods and embodiments, it will be appreciated that various modifications and changes may be made without departing from the invention.

It is claimed:

1. A method of preventing or treating hyperproliferative vascular disease in a susceptible mammal, comprising
administering to said mammal an amount of mycophenolic acid effective to i it intimal thickening in said mammal.

2. The method of claim 1, wherein the administering is accomplished orally, parenterally, intravascularly, intranasally, intrabronchially, transdermally, rectally, or via a vascular stent impregnated with mycophenolic acid.

3. The method of claim 1, wherein the mycophenolic acid is administered concurrent with said mammal undergoing a percutaneous transluminal coronary angioplasty procedure.

4. The method of claim 3, which further comprises administering the mycophenolic acid subsequent to said mammal undergoing a percutaneous transluminal coronary angioplasty procedure.

5. The method of claim 1, wherein the hyperproliferative vascular disease is selected from the group consisting of intimal smooth muscle cell hyperplasia, restenosis, and vascular occlusion.

6. The method of claim 5, wherein the hyperproliferative vascular disease is restenosis.

7. The method of claim 6, wherein the mycophenolic acid which is selected is in the form of a pharmaceutically acceptable salt.

8. The method of claim 1, wherein the mycophenolic acid is administered prior to, concurrent with and/or subsequent to said mammal sustaining a biologically mediated vascular injury.

9. The method of claim 1, wherein the mycophenolic acid is administered prior to, concurrent with and/or subsequent to said mammal sustaining a mechanically mediated vascular injury.

* * * * *